United States Patent [19]

Schulze et al.

[11] 4,290,963
[45] Sep. 22, 1981

[54] PROCESS FOR PREPARING $\Delta^{9(11)}$ AND/OR $\Delta^{16}$-UNSATURATED STERNOIDS

[75] Inventors: Paul-Eberhard Schulze; Ulrich Kerb, both of Berlin, Fed. Rep. of Germany

[73] Assignee: Schering Aktiengesellschaft, Berlin, Fed. Rep. of Germany

[21] Appl. No.: 170,210

[22] Filed: Jul. 18, 1980

[30] Foreign Application Priority Data

Jul. 18, 1979 [DE] Fed. Rep. of Germany ....... 2929558

[51] Int. Cl.³ .............................................. C07J 5/00
[52] U.S. Cl. ................................................ 260/397.45
[58] Field of Search .................................... 260/397.45

[56] References Cited

U.S. PATENT DOCUMENTS 4,061,661 12/1977 Kerb et al. .................... 260/397.45
4,064,148 12/1977 Barton et al. .................. 260/397.45

OTHER PUBLICATIONS

Breslow et al., "JACS" (1977) vol. 99 pp. 905–915 relied on.

Primary Examiner—Elbert L. Roberts
Attorney, Agent, or Firm—Millen & White

[57] ABSTRACT

A process for preparing a $\Delta^{9(11)}$- and/or $\Delta^{16}$-unsaturated steroid comprises heating the corresponding steroid of the pregnane series substituted by 9α-chloro- and/or 16α-chloro- or 17α-acyloxy, in an inert, aprotic high-boiling solvent at 180°–350° C.

10 Claims, No Drawings

PROCESS FOR PREPARING $\Delta^{9(11)}$ AND/OR $\Delta^{16}$-UNSATURATED STERNOIDS

BACKGROUND OF THE INVENTION

The present invention relates to a process for preparing $\Delta^{9(11)}$- and/or $\Delta^{16}$-unsaturated steroids.

As is known, $\Delta^{9(11)}$-unsaturated steroids can be prepared from the corresponding 11β- or α-alcohols by conversion into the sulfonates (e.g. mesylates) and elimination of these esters under alkaline conditions (P. Wieland et al., Helv. 43: 523 [1960]), or, after blocking the carbonyl groups, with phosphorus oxychloride in pyridine (S. Bernstein et al., JACS 75: 4830 [1953]).

It is furthermore known that $\Delta^{16}$-unsaturated steroids of the pregnane series can be obtained from the corresponding 17α-hydroxy-20-ketopregnanes by treatment with phosphorus oxychloride in pyridine at room temperature (Fried & Edwards, Organic Reactions in Steroid Chemistry, II: 171 [1972]).

These conventional chemical methods, however, are disadvantageous in that they either proceed by way of several stages or provide unsatisfactory yields.

SUMMARY OF THE INVENTION

Accordingly, it is an object of this invention to provide a process for preparing $\Delta^{9(11)}$- or $\Delta^{16}$-unsaturated steroids which lack such disadvantages.

Upon further study of the specification and appended claims, further objects and advantages of this invention will become apparent to those skilled in the art.

These objects have been attained by this invention by providing a process for preparing a $\Delta^{9(11)}$- and/or $\Delta^{16}$-unsaturated steroid from the corresponding 9α-chloro, and/or 16α-chloro or 17α-acyloxy steroid e.g., of the pregnane series, by heating the starting steroid in an inert, aprotic high-boiling solvent to 180°-350° C., preferably 200°-300° C.

DETAILED DESCRIPTION

The results of the reaction of this invention are surprising insofar as it was to be expected that undesired thermal decompositions and rearrangements would occur when heating the starting steroids to temperature above their melting points. However, instead, compounds of steric integrity are produced.

Suitable acyloxy groups in the 17α-position of the starting material steroids include those acid residues derived from alkanoic acids of up to 10, preferably of up to 6 carbon atoms, and from aromatic acids of 7-11 carbon atoms, which can also optionally be substituted by lower alkyl (e.g., of 1-4 C atoms) or halogen, such as chlorine or iodine. Examples include acetic, propionic, isobutyric, valeric, caproic, and m-iodobenzoic acids.

The process of this invention is applicable to starting material steroids having a 17α-acyloxy substituent only; a 16α-chloro substituent only; or a combination of a 17α-acyloxy and a 9α-chloro substituent.

In general, it is easier to achieve unsaturation by the elimination of the chloro substituent in the 9α- and 16α-position than by the elimination of the 17α-acyloxy substituent. Accordingly, by suitable selection of more moderate reaction conditions, i.e., lower temperatures, such as 180°-240° C., the 9(11)-position can be selectively unsaturated while the 16-position remains saturated when a 17α-acyloxy substituent is present in the molecule. If desired, further reaction at a higher temperature, e.g., 240°-300° C., can be used to effect subsequent unsaturation at the 16-position. Further, if simultaneous unsaturation at both the 9(11) and 16 positions is desired when the combination of a 17α-acyloxy and 9α-chloro is present, this can be achieved by conduction of the reaction at the higher mentioned temperature range.

The starting material steroids which may be utilized in this invention are particularly of the pregnane series. The side chains thereof in the 17β-position can also be unsaturated. These compounds can even be further substituted. Examples of suitable substituents include lower alkyl (e.g., of 1-4 C atoms), such as methyl, in the 2-, 6-, 16-, 18- and 21- positions; halogen, such as chlorine, in the 2-, 6- and 12-positions; and hydroxy in the 3- or 11-position. Likewise present can be alkynyl, such as ethynyl, in the 17-position, and keto in the 3-, 11- and 20-positions. Methylene can be in the 1,2- or 6,7-position. Double bonds can be in the 1-, 4-, 5- and 6-positions. Additional acyloxy groups can occur in the 3- and/or 21-position. In particular, the lower alkyl groups and halogen atoms can be present on carbon atoms wich are part of a double bond, such as in the grouping $\Delta^6$-6-chloro.

Suitable solvents for conducting the process of this invention include inert, high-boiling aprotic solvents e.g., boiling points of 200°-400° C., such as, for example, biphenyl, diphenylene oxide, dibenzyl benzene, oligoglycol dimethyl ethers, such as di-, tri-, and polyglycol 200 dimethyl ethers, and mixtures of these compounds. These liquids are, in part, commercially available. Under the name "Dowtherm" A, a eutectic mixture of biphenyl and dibenzofuran (approximate b.p. 285° C.) can be obtained; under the name "Marlotherm" S, dibenzyl benzene isomeric mixtures (approximate b.p. 390° C.) is obtainable; and under the designation "Polyglycol 200 Dimethyl Ether" a homologous mixture of pentaethylene glycol dimethyl ether is available, $CH_3O(CH_2CH_2O)_nCH_3$, n=2-10 (boiling range 240°-350° C.).

The solvent is utilized in a quantity of 2-50 parts by weight, preferably 5-20 parts by weight, per weight part of starting material.

The process of this invention may be conducted by dissolving the starting material in the solvent, and heating over a period of 5-100 minutes at temperatures of 180°-350° C., preferably 200°-300° C. It is advantageous to heat the reaction mixture under a protective inert gas atmosphere, such as, for example, nitrogen, to exclude the influence of oxygen. Also advantageous is the introduction of the solid compound under a protective gas into the solvent, which latter has previously been brought to the desired temperature. The course of the thermolysis can be readily controlled by thinlayer chromatography. After the reaction is finished, the reaction mixture is cooled and worked up as usual, such as by filtration, washing, and elution. A preferred working-up method is the removal of the solvent by steam distillation, drying of the residue, and recrystallization.

From a general viewpoint, the process of this invention has the advantage that it requires only an exceedingly simple manipulation. The compound is heated in the solvent and, after the reaction, is again separated from the solvent. An additional advantage of the process is derived from the fact that split-off hydrogen chloride or readily volatile organic acids escape from the reaction liquid during heating. Thus, no neutralization is required. Acid-catalyzed rearrangements, such as, for example, the dienone phenol rearrangement of Δ$^{1,4}$-3-keto steroids, cannot occur ab initio.

A further advantage over the otherwise customary process of hydrogen chloride elimination from 9α-chloro steroids by means of silver perchlorate with the formation of the corresponding Δ$^{9(11)}$-compounds, results from the lack of use of dangerous substances, such as the aforementioned silver perchlorate.

The compounds producible by the process of this invention can be used as starting compounds for the preparation of known active agents, e.g., corresponding steroids which are functionalized via reaction with the Δ$^{9(11)}$ or Δ$^{16}$ double bonds. Thus, it is possible, for example, to prepare prednisolone from 3β-hydroxy-5,16-pregnadien-20-one, and, after introduction of a 16α-positioned methyl group, fluocortolone, clocortolone, and diflucortolone. From the corresponding 21-functionalized Δ$^{16}$-unsaturated 3,20-ketopregnenes, it is thus possible to produce conventional corticoids, such as triamcinolone, dexamethasone and betamethasone. Furthermore, it is possible to prepare conventional 9α-halo hydrocortisone and prednisolone from Δ$^{9(11)}$-unsaturated compounds of this invention by addition of hypobromic acid, conversion to the 9β,11β-epoxide and ring opening with the respective halo hydrogen acid.

Without further elaboration, it is believed that one skilled in the art can, using the preceding description, utilize the present invention to its fullest extent. The following perferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

One gram of 17α-acetoxy-11β-benzoyloxy-1α,2α-methylene-4,6-pregnadiene-3,20-dione is dissolved in 10 ml of "Dowtherm" (filtered over Al$_2$O$_3$). The solution is heated under a stream of nitrogen gas for 30 minutes to 285° C. After cooling, the mixture is diluted with hexane, introduced into a silica gel column, and the "Dowtherm" is eluted with hexane. The thus-prepared compound is now eluted with methylene chloride and a gradually increasing proportion of chloroform. The individual fractions are tested for content and purity by thin-layer chromatography. The fractions having the desired compound are combined, concentrated, and the residue is recrystallized from benzene, thus obtaining 700 mg of 11β-benzoyloxy-1α,2α-methylene-4,6,16-pregnatriene-3,20-dione (79% of theory), m.p. 227°–229° C.

EXAMPLE 2

One gram of 17α-acetoxy-1α,2α-methylene-11β-hydroxy-4,6-pregnadiene- 3,20-dione is heated analogously to Example 1 in "Marlotherm" for 60 minutes to 285° C., worked up, separated, and combined. After recrystallization from ethanol, 780 mg of 1α,2α-methylene-11β-hydroxy-4,6,16-pregnatriene-3,20-dione (81% of theory) is obtained, m.p. 245°–248° C.

EXAMPLE 3

One gram of 17α-acetoxy-6-chloro-1α,2α-methylene-4,6-pregnadiene-3,20-dione is heated analogously to Example 1 in "Dowtherm" for 90 minutes to 285° C., worked up, separated, and combined. Recrystallization from ethanol yields 380 mg of 6-chloro-1α,2α-methylene-4,6,16-pregnatriene-3,20-dione (89% of theory), m.p. 243°–246° C.

EXAMPLE 4

One gram of 17α-hexanoyloxy-4pregnene-3,20-dione is heated analogously to Example 1 in "Dowtherm" for 80 minutes to 285° C., worked up, separated, and combined. Recrystallization from ethanol yields 600 mg of 4,16-pregnadiene-3,20-dione (83% of theory), m.p. 185°–190° C.

EXAMPLE 5

One gram of 17α,21-diacetoxy-4-pregnene-3,20-dione is heated analogously to Example 1 in "Dowtherm" for 80 minutes to 285° C., worked up, separated, and combined. Recrystallization from hexane/ethyl acetate yields 700 mg of 21-acetoxy-4,16-pregnadiene-3,20-dione (83% of theory), m.p. 146°–148° C.

EXAMPLE 6

One gram of 3β,17α-diacetoxy-5-pregnen-20-one is heated analogously to Example 1 in "Dowtherm" for 40 minutes to 285° C. and worked up. Recrystallization from ethanol yields 700 mg of 3β-acetoxy-5,16-pregnadien-20-one (80% of theory), m.p. 169°–172° C.

EXAMPLE 7

One gram of 17α-hexanoyloxy-19-nor-4-pregnene-3,20-dione is treated analogously to Example 1 in "Dowtherm" for 70 minutes at 280° C. and worked up. Recrystallization from isopropyl ether yields 650 mg of 19-nor-4,16-pregnadiene-3,20-dione (93% of theory), m.p. 163°–166° C.

EXAMPLE 8

One gram of 21-acetoxy-17α-(3'-iodobenzoyloxy)-4-pregnene-3,20-dione is treated analogously to Example 1 in "Dowtherm" for 15 minutes at 250° C. and worked up. Recrystallization from isopropyl ether yields 670 mg of 21-acetoxy-4,16-pregnadiene-3,20-dione (93% of theory).

UV (methanol): $\epsilon_{241}$=24,000.

EXAMPLE 9

One gram of 17α,21-diacetoxy-11β-hydroxy-1,4-pregnadiene-3,20-dione is treated analogously to Example 1 in "Dowtherm" for 50 minutes at 250° C. and worked up. Recrystallization from isopropyl ether yields 700 mg of 21-acetoxy-11β-hydroxy-1,4,16-pregnatriene-3,20-dione (81% of theory).

UV (methanol): $\epsilon_{242}$=22,500.

EXAMPLE 10

One gram of 17α-acetoxy-17β-ethynyl-4-estren-3-one is treated analogously to Example 1 in "Dowtherm" for 10 minutes at 250° C. and worked up. Recrystallization from isopropyl ether yields 500 mg of 17-ethynyl-4,16-estradien-3-one, m.p. 148°–152° C. (40% of theory).

UV: $\epsilon_{236}$=23,000.

EXAMPLE 11

One gram of 17α-acetoxy-12α-chloro-1α,2α-methylene-4,6-pregnadiene-3,20-dione is treated analogously to Example 1 in "Dowtherm" for 1 hour at 280° C. and worked up. Recrystallization from isopropyl ether yields 500 mg of 12α-chloro-1α,2α-methylene-4,6,16-pregnatriene (61% of theory).

UV: $\epsilon_{235} = 12{,}150$; $\epsilon_{281} = 15{,}800$.

EXAMPLE 12

One gram of 3β-acetoxy-16α-chloro-5-pregnen-20-one is treated analogously to Example 1 in "Dowtherm" for 6 hours at 240° C. and worked up. Recrystallization from isopropyl ether yields 400 mg of 3β-acetoxy-5,16-pregnadien-20-one (56% of theory).

UV: $\epsilon_{239} = 6{,}400$.

EXAMPLE 13

2.4 g of 17,21-bis(3-iodobenzoyloxy)-1,4-pregnadiene-3,20-dione is stirred in 15 ml of "Dowtherm" under argon for 40 minutes at an oil bath temperature of 260° C. After cooling, the mixture is diluted with methylene chloride, the thus-crystallized iodobenzoic acid is vacuum-filtered, and the filtrate is chromatographed on silica gel. With toluene-nitromethane, 1.2 g of 21-(3-iodobenzoyloxy)-pregna-1,4,16-triene-3,20-dione (72% of theory) is eluted, m.p. 168°–169° C.

EXAMPLE 14

1.3 g of 9α-chloro-21-acetoxy-17α-(3-iodobenzoyloxy)-4-pregnene-3,20-dione is stirred in 10 ml of "Dowtherm" under argon for 20 minutes at an oil bath temperature of 220° C. During this step, the thus-formed product is crystallized. After cooling, the mixture is diluted with methylene chloride and chromatographed on silica gel. With toluene-ether, the 21-acetoxy-17α-(3-iodobenzoyloxy)pregna-4,9(11)-diene-3,20-dione is eluted and recrystallized from methylene chloride-ethyl acetate, m.p. 257°–260° C. Yield: 79% of theory.

EXAMPLE 15

616 mg of 21-acetoxy-17α-(3-iodobenzoyloxy)pregna-4,9(11)-diene-3,20-dione is stirred in 5 ml of "Dowtherm" for 20 minutes at a bath temperature of 260° C. and chromatographed analogously to Example 1, thus obtaining in a 60% yield 21-acetoxypregna-4,9(11),16-triene-3,20-dione, m.p. 128°–129° C. (ether).

EXAMPLE 16

300 mg of 9α-chloro-17,21-bis(3-iodobenzoyloxy)-1,4-pregnadiene-3,20-dione is stirred in 2 ml of "Dowtherm" for 40 minutes at 260° C. oil bath temperature and chromatographed, thus obtaining 21-(3-iodobenzoyloxy)-1,4,9(11),16-pregnatetraene-3,20-dione, m.p. 151°–152° C. (acetone-hexane). Yield: 74% of theory.

EXAMPLE 17

1.3 g of 9α-chloro-21-acetoxy-17α-(3-iodobenzoyloxy)-4-pregnene-3,20-dione is stirred in 10 ml of "Dowtherm" under argon for 15 minutes at an oil bath temperature of 280° C. Chromatography on silica gel yields 518 mg of 21-acetoxypregna-4,9(11),16-triene-3,20-dione (70% of theory), m.p. 127°–129° C.

EXAMPLE 18

Analogously to Example 1, the following compounds are prepared under the indicated reaction conditions:

| | Final Product | Starting Material | Temp. [°C.] | Time [min] | Yield [%] |
|---|---|---|---|---|---|
| a | 11β-Hydroxy-21-acetoxy-pregna-1,4,16-triene-3,20-dione | 11β-Hydroxy-17α,21-diacetoxy-pregna-1,4-diene-3,20-dione | 250 | 50 | 78 |
| b | 3β-Hydroxy-pregna-5,16-dien-20-one | 3β-Hydroxy-17α-acetoxy-5-pregnen-20-one | 285 | 40 | 74 |
| c | 3,20-Diketo-pregna-4,16-diene | 17α-Acetoxy-4-pregnene-3,20-dione | 285 | 50 | 80 |
| d | 11β-Hydroxy-pregna-4,6,16-triene-3,20-dione | 11β-Hydroxy-17α-acetoxy-pregna-4,6-diene-3,20-dione | 285 | 90 | 88 |

EXAMPLE 19

1.19 g of 9α-chloro-17α-(3-iodobenzoyloxy)-4-pregnene-3,20-dione is stirred in 10 ml of polyglycol 200 dimethyl ether for 20 minutes at an oil bath temperature of 280° C. under argon. After cooling, the mixture is poured into an ice-cold sodium bicarbonate solution; the precipitated product is vacuum-filtered and dried. Recrystallization from methanol yields 580 mg of 4,9(11),16-pregnatriene-3,20-dione, m.p. 200°–201° C. (yield: 93% of theory).

EXAMPLE 20

5.95 g of 9α-chloro-17α-(3-iodobenzoyloxy)-4-pregnene-3,20-dione is stirred in 30 ml of "Dowtherm" under argon gas for 20 minutes at an oil bath temperature of 280° C. After filtration over silica gel and recrystallization from methanol, 2.92 g of 4,9(11),16-pregnatriene-3,20-dione is obtained, m.p. 200.5°–201.5° C. (yield: 94% of theory).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a $\Delta^{9(11)}$-and/or $\Delta^{16}$-unsaturated steroid of the pregnane series which consists essentially of heating the corresponding 9,11- and/or 16- saturated steroid substituted by 17α-acyloxy, 16α-chloro or 17α-acyloxy and 9α-chloro, in an inert, aprotic high-boiling solvent at 180°–350° C.

2. The process of claim 1 wherein the corresponding starting material steroid of the pregnane series is heated to 200°–300° C.

3. The process of claim 1 wherein the corresponding starting material steroid is heated in an inert atmosphere.

4. The process of claim 1 wherein the amount of solvent is 2–50 weight parts per weight part of corresponding starting material steroid.

5. The process of claim 1 wherein the corresponding starting material steroid is substituted by 17α-acyloxy.

6. The process of claim 5 wherein the 17α-acyloxy group is $C_{1-10}$ alkanoyloxy, benzoyloxy or benzoyloxy substituted by lower alkyl or halogen.

7. The process of claim 5 wherein the 17α-acyloxy substituent is acetoxy or 3-iodobenzoyloxy.

8. The process of claim 5 wherein the corresponding starting material steroid is also substituted by 9α-chloro.

9. The process of claim 8 wherein the starting material steroid is substituted by a 9α-chloro substituent and a 17α-acyloxy substituent and the reaction temperature is 180°–240° C., whereby only the 9(11)-position becomes unsaturated in the product steroid.

10. The process of claim 9 wherein the resultant product steroid is further heated at a temperature of 240°–300° C. whereby the 16-position also becomes unsaturated.

* * * * *